(12) United States Patent
Stelzer et al.

(10) Patent No.: US 8,219,184 B2
(45) Date of Patent: Jul. 10, 2012

(54) APPARATUS FOR MEASURING, RECORDING AND TRANSMITTING ELECTROCARDIOGRAM MEASUREMENTS

(75) Inventors: Gunter Stelzer, Grebenhain (DE); Vincent DiGregorio, Garden City, NY (US); Hans Zobel, Water Mill, NY (US); Ian Warburton, Poquott, NY (US)

(73) Assignee: Ziehm Imaging GmbH, Nuremberg (DE)

( * ) Notice: Subject to any disclaimer, the term of this patent is extended or adjusted under 35 U.S.C. 154(b) by 621 days.

(21) Appl. No.: 12/392,632

(22) Filed: Feb. 25, 2009

(65) Prior Publication Data

US 2009/0216142 A1 Aug. 27, 2009

Related U.S. Application Data

(60) Provisional application No. 61/031,063, filed on Feb. 25, 2008.

(51) Int. Cl.
*A61B 5/0402* (2006.01)

(52) U.S. Cl. ........................................ 600/509

(58) Field of Classification Search ........... 600/509, 600/520, 513
See application file for complete search history.

(56) References Cited

U.S. PATENT DOCUMENTS

| | | | |
|---|---|---|---|
| 2,149,690 A | 3/1939 | Snyder | |
| 3,857,383 A | 12/1974 | Sommerfeld et al. | |
| 3,960,141 A | 6/1976 | Bolduc | |
| 4,267,490 A * | 5/1981 | Thiene | 318/51 |
| 4,328,814 A | 5/1982 | Arkans | |
| 4,491,725 A | 1/1985 | Pritchard | |
| 4,518,052 A | 5/1985 | Chen | |
| 4,583,549 A | 4/1986 | Manoli | |
| 4,643,193 A | 2/1987 | DeMarzo | |
| 4,838,275 A | 6/1989 | Lee | |
| 5,042,498 A | 8/1991 | Dukes | |
| 5,111,539 A | 5/1992 | Hiruta et al. | |
| 5,193,541 A | 3/1993 | Hatsuwi | |
| 5,309,918 A * | 5/1994 | Schraag | 600/508 |
| 5,410,471 A | 4/1995 | Alyfuku et al. | |
| 5,441,047 A | 8/1995 | David et al. | |
| 5,442,728 A | 8/1995 | Kaufman et al. | |
| 5,505,218 A * | 4/1996 | Steinhauser et al. | 134/95.1 |
| 5,544,649 A | 8/1996 | David et al. | |
| 5,590,648 A | 1/1997 | Mitchell et al. | |
| 5,678,545 A | 10/1997 | Stratbucker | |
| 5,697,376 A | 12/1997 | Nomura et al. | |
| 5,748,907 A | 5/1998 | Crane | |
| 5,795,403 A * | 8/1998 | Biermaier | 134/22.12 |
| 5,865,741 A | 2/1999 | Kelly et al. | |
| 5,916,159 A | 6/1999 | Kelly et al. | |
| 5,974,124 A | 10/1999 | Schlueter, Jr. et al. | |
| 6,006,125 A | 12/1999 | Kelly et al. | |
| 6,018,677 A | 1/2000 | Vidrine et al. | |
| 6,046,761 A | 4/2000 | Echerer | |

(Continued)

FOREIGN PATENT DOCUMENTS

JP 2000194790 6/2009

*Primary Examiner* — George Evanisko
(74) *Attorney, Agent, or Firm* — Hoffmann & Baron, LLP

(57) ABSTRACT

Embodiments of the present invention include a monitoring device and method for measuring, recording and transmitting a pre-determined set of electrocardiogram measurements. The device provides for an unassisted six or twelve channel measurements of heart and vascular functions using a visual graphical output. Results of the measurements are charted and can be reviewed and analyzed by an authorized health care provider.

17 Claims, 17 Drawing Sheets

U.S. PATENT DOCUMENTS

| | | | |
|---|---|---|---|
| 6,066,093 A | 5/2000 | Kelly et al. | |
| 6,093,156 A | 7/2000 | Cunningham et al. | |
| 6,101,478 A | 8/2000 | Brown | |
| 6,157,851 A | 12/2000 | Kelly et al. | |
| 6,203,106 B1 | 3/2001 | Nearing et al. | |
| 6,205,716 B1 | 3/2001 | Peltz | |
| 6,319,207 B1 | 11/2001 | Naidoo | |
| 6,336,900 B1 | 1/2002 | Alleckson et al. | |
| 6,398,740 B1 | 6/2002 | Lavery et al. | |
| 6,400,977 B1 | 6/2002 | Kelly et al. | |
| 6,403,897 B1 | 6/2002 | Bluth et al. | |
| 6,409,661 B1 | 6/2002 | Murphy | |
| 6,415,188 B1 | 7/2002 | Fernandez et al. | |
| 6,428,124 B1 | 8/2002 | Bluth et al. | |
| 6,497,657 B2 | 12/2002 | Nunome | |
| 6,511,435 B1 | 1/2003 | Bluth et al. | |
| 6,524,240 B1 | 2/2003 | Thede | |
| 6,553,246 B1 | 4/2003 | Wenger | |
| 6,560,473 B2 | 5/2003 | Dominguez | |
| 6,594,607 B2 | 7/2003 | Lavery | |
| 6,619,746 B2 | 9/2003 | Roslund, Jr. et al. | |
| 6,692,436 B1 | 2/2004 | Bluth et al. | |
| 6,705,990 B1 * | 3/2004 | Gallant et al. | 600/300 |
| 6,751,493 B2 | 6/2004 | Wenger | |
| 6,767,330 B2 | 7/2004 | Lavery et al. | |
| 6,781,067 B2 | 8/2004 | Montagnino et al. | |
| 6,800,059 B2 | 10/2004 | Muraki et al. | |
| 6,832,987 B2 * | 12/2004 | David et al. | 600/300 |
| 6,842,722 B2 | 1/2005 | David | |
| 6,922,664 B1 | 7/2005 | Fernandez et al. | |
| 6,980,853 B2 | 12/2005 | Miyoshi et al. | |
| 7,038,588 B2 | 5/2006 | Boone et al. | |
| 7,039,457 B2 | 5/2006 | Young et al. | |
| 7,066,890 B1 | 6/2006 | Lam et al. | |
| 7,158,030 B2 | 1/2007 | Chung | |
| 7,163,516 B1 | 1/2007 | Pagnacco et al. | |
| 7,191,075 B2 | 3/2007 | Shimizu | |
| 2001/0027270 A1 | 10/2001 | Stratbucker | |
| 2001/0039504 A1 | 11/2001 | Linberg et al. | |
| 2002/0026333 A1 | 2/2002 | Endou | |
| 2002/0029157 A1 | 3/2002 | Marchosky | |
| 2002/0123679 A1 | 9/2002 | Dominguez | |
| 2003/0176948 A1 | 9/2003 | Green | |
| 2004/0044560 A1 | 3/2004 | Giglio et al. | |
| 2004/0049355 A1 | 3/2004 | Maus et al. | |
| 2004/0138924 A1 | 7/2004 | Pristine | |
| 2005/0130295 A1 | 6/2005 | Li | |
| 2006/0010007 A1 | 1/2006 | Denman et al. | |
| 2006/0047188 A1 | 3/2006 | Bohan | |
| 2006/0111620 A1 | 5/2006 | Squilla et al. | |
| 2006/0195564 A1 | 8/2006 | Accardi et al. | |
| 2006/0290885 A1 | 12/2006 | Covannon et al. | |
| 2007/0073113 A1 | 3/2007 | Squilla et al. | |
| 2007/0129610 A1 | 6/2007 | Squilla | |
| 2007/0143151 A1 | 6/2007 | Fey et al. | |

* cited by examiner

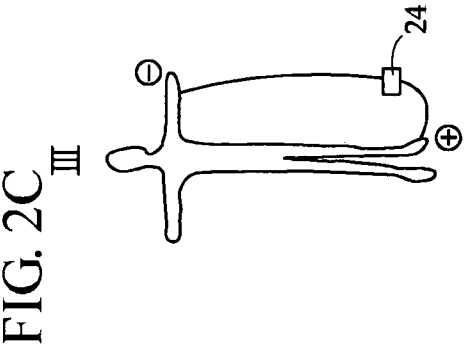
FIG. 2A  FIG. 2B  FIG. 2C
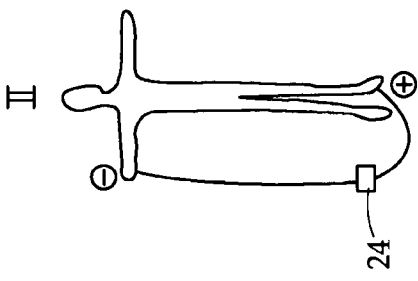
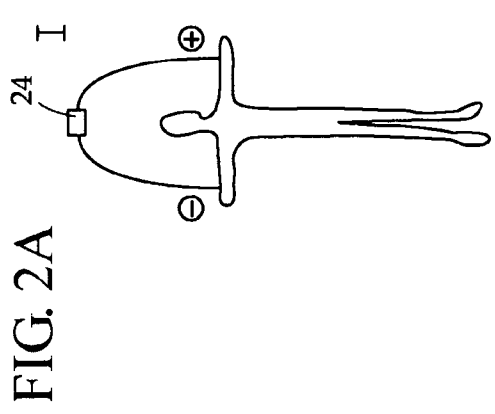
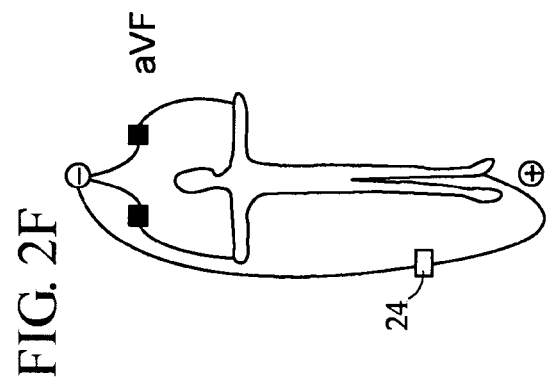
FIG. 2D  FIG. 2E  FIG. 2F
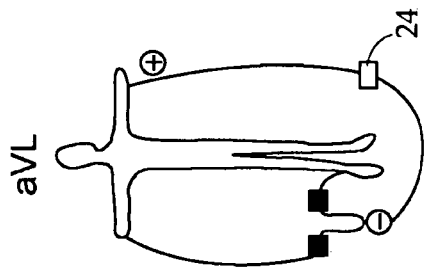
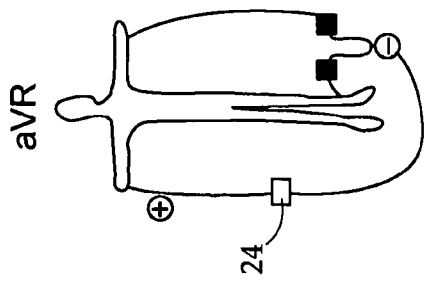

APPARATUS FOR MEASURING, RECORDING AND TRANSMITTING ELECTROCARDIOGRAM MEASUREMENTS

CROSS-REFERENCE TO RELATED APPLICATION

The present application claims priority to U.S. Provisional Patent Application Ser. No. 61/031,063 filed Feb. 25, 2008, the disclosure of which is incorporated herein by reference in its entirety.

BACKGROUND

1. Field of Technology

The present invention generally relates to electrocardiogram measurements and more particularly to a device for measuring, recording and transmitting electrocardiogram measurements.

2. Brief Description of the Related Art

Generally, an electrocardiogram (ECG) procedure is performed with several electrical connections, such as independently applied transducers, that are attached to an array of measurement points on an upper torso (thorax) and/or lower legs of a patient.

Typically, a medical attendant first abrades each area of the patient's skin to which an electrical connection is to be applied and then wipes the same area with an alcohol cleaning swab. The attendant then applies a small amount of electrically-conductive gel to the surface of the patient's skin to provide an effective electrical connection between the connectors and the skin surface. Next, the attendant applies at each of the measurement points a disposable self-adhesive patch and connector that positioned on the target area. Finally, the attendant connects each of the patches to the appropriate ECG measurement lead. In some embodiments, to aid correct connection, each of the ECG leads is color coded and connected to an ECG analyzer unit. In the case of hirsute patients, the attendant typically shaves the target areas first to remove any excess hair that can interfere with the patch.

There are several drawbacks in using the above-mentioned ECG technique. For example, the above described technique requires a medical attendant to be present during the procedure and to prepare the patient and equipment prior to commencing the procedure. In addition, the use of electrically-conductive gel tends to be untidy and uncomfortable for patients. Furthermore, the accuracy of ECG measurements can vary based on the location of electrical connections on the patient.

Accordingly, it would be desirable to provide an improved method and device for performing an ECG procedure.

SUMMARY

The present invention relates to a monitoring device and method for measuring, recording and transmitting a pre-determined set of electrocardiogram (ECG) measurements. The monitoring device provides for an unassisted completion of measurements of heart and vascular functions using a visual graphical output. Results of the measurements can be charted for review and analysis by an authorized health care provider.

Various aspects of the invention relate to measuring and recording ECG signals received from a patient. For example, according to one aspect, an ECG measuring device that includes an electrically adjustable support structure, hand grips, foot plates, and an ECG analyzer unit is disclosed. The hand grips are operatively coupled to the support structure and a patient is seated on the support structure during an ECG measurement. The hand grips and foot plates include tactile-sensing ECG transducers. The hand grips can have at least one of a spherical, hemispherical, and bar-like configuration. The hand grips and foot plates are spaced apart from each other and are engageable with a patient during an ECG measurement. The ECG analyzer unit is in communication with the hand grips and the foot plates to receive ECG signals from the patient in contact with the transducers. The ECG analyzer unit is configured to chart ECG information received from the transducers. At least one of the ECG transducers can be made from silver silver chloride (Ag—AgCl).

The support structure can include an arm rest configured to include at least one of the hand grips. In some embodiments, a hinged arm can be operatively connected to the support structure. The hinged arm includes a plurality of tactile-sensing ECG transducers in communication with the ECG analyzer unit and is configured to engage a thoracic region of a patient during the ECG measurement. The tactile sensing transducers of the hinged arm are disposed on an inflatable cell, the inflatable cell inflating during the ECG measurement to force the tactile sending transducers of the hinged arm outward and away from the hinged arm to facilitate sufficient contact between the tactile-sensing transducers and the patient for performing the ECG measurement.

The support structure can include a back rest extending from the seat in a substantially vertical manner and a longitudinally extending shaft disposed on a side of the back rest. The hinged arm can be operatively coupled to the shaft by engaging a channel formed in the shaft to facilitate vertical movement of the hinged arm along the channel. The hinged arm is configured to pivot radially about the shaft. The hinged arm includes a locking device for securing the hinged arm in a measurement position and retaining a patient between the back rest and the hinged arm to facilitate contact between the tactile-sensing transducers of the hinged arm and the thorax of the patient.

In some embodiments, the ECG measuring device can include a video display unit to display information to the patient and at least one speaker to communicate audio information to the patient. The ECG measuring device can also include a cleaning unit in proximity with the foot plates. The cleaning unit can apply a cleaning fluid to at least one of the foot plates to substantially disinfect the at least one of the foot plates upon completion of the measurement.

In some embodiments, the hand grips are pivotally coupled to an underside of the seat via arms. The hand grips can be configured to be pivotally positioned about the seat and the arm can have a telescopic configuration to facilitate lateral extension of the hand grips away from the seat.

In yet another aspect of the invention, a method of measuring and recording electrocardiographic (ECG) signals is disclosed. The method includes providing a support structure on which a patient is seated. The support structure is electrically adjustable by the patient. The method also includes adjusting, electrically, a position of the support structure in response to input from the patient, where the support structure includes hand grips that are operatively coupled to the support structure. The method also includes acquiring ECG information representing a heart function of a patient from a plurality of hand grips in contact with hands of the patient and from a plurality of foot plates in contact with feet of the patient. The hand grips and foot plates include tactile-sensing ECG transducers and the foot plates and hand grips are spaced apart from each other. The method further includes storing the ECG information to a database and charting the ECG information received from the hand grips and foot plates to display a result of the ECG measurement.

In some embodiments acquiring ECG information representing a heart function of a patient includes acquiring ECG information from a plurality of tactile-sensing ECG transducers disposed on a hinged arm engageable with a thoracic region of the patient during the ECG measurement.

The method can also include reading patient information from a patient ID card before commencement of the ECG measurement, associating the result with the patient information read from the patient ID card, and/or transmitting the electrocardiographic signals to a host computer that displays the result of the ECG measurement. The method can further include applying a cleaning fluid to at least one of the ECG transducers upon completion of the measurement.

Several advantages stem from use of the present invention. For example, the invention can replace the need for a medical attendant to be present during an ECG procedure. Instead, in one preferred embodiment, the patient can be prompted by visual and audio instructions to sit in a chair provided, remove their shoes, socks/stockings and place their feet on metal plates on the floor and grasp metal spheres in order to obtain an ECG measurement.

Advantageously, the present invention does not require any additional electrical conducive gel on the plates or the spheres.

Another advantage relates to hygiene. For example, either at the commencement of the test or after completion, an automated spray of standard and approved cleaning fluid can be applied to either or both the foot plates and hand grips. Advantageously, this can reduce the risk of cross-contamination from patient to patient and the cleaning agent can evaporate in normal ambient temperatures prior to the next patient's use.

Other objects and features of the present invention will become apparent from the following detailed description considered in conjunction with the accompanying drawings. It is to be understood, however, that the drawings are designed as an illustration only and not as a definition of the limits of the invention.

BRIEF DESCRIPTION OF THE DRAWINGS

FIGS. 2A-F illustrate example connections for ECG analysis using the device shown in FIGS. 1A-C;

Like reference symbols in the various drawings indicate like elements.

DETAILED DESCRIPTION

Embodiments of present invention include a monitoring device and method for measuring, recording and transmitting a pre-determined set of electrocardiogram (ECG) measurements. The monitoring device facilitates unassisted measurements of heart and vascular functions using a visual graphical output. The results of the measurements are charted and can be reviewed and analyzed by an authorized health care provider. In some embodiments, a twelve channel ECG measurement can be performed.

Figure 1A:
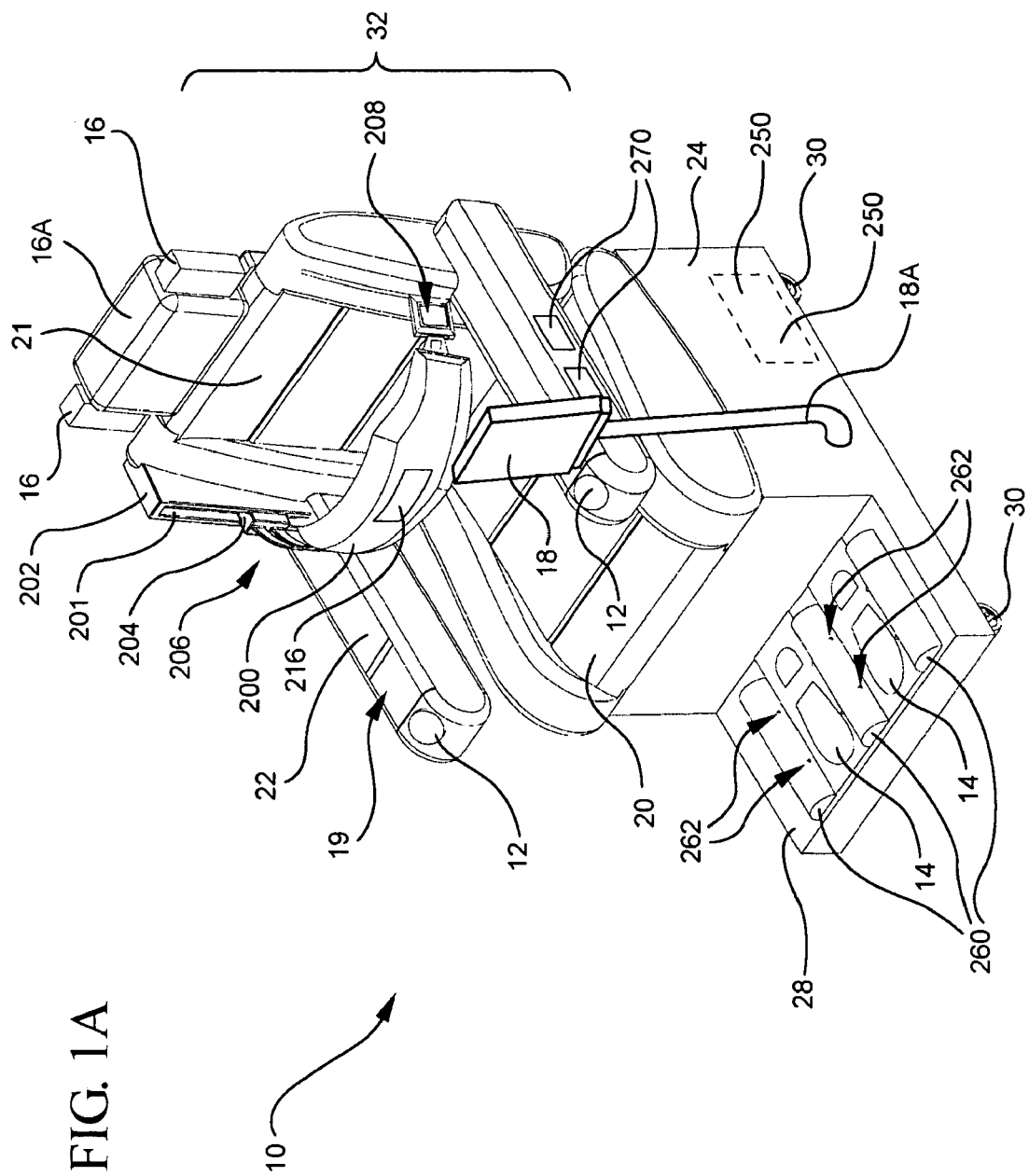
FIGS. 1A-C illustrate perspective views of an ECG measuring device according to a first embodiment of the present invention.
Figure 1B:
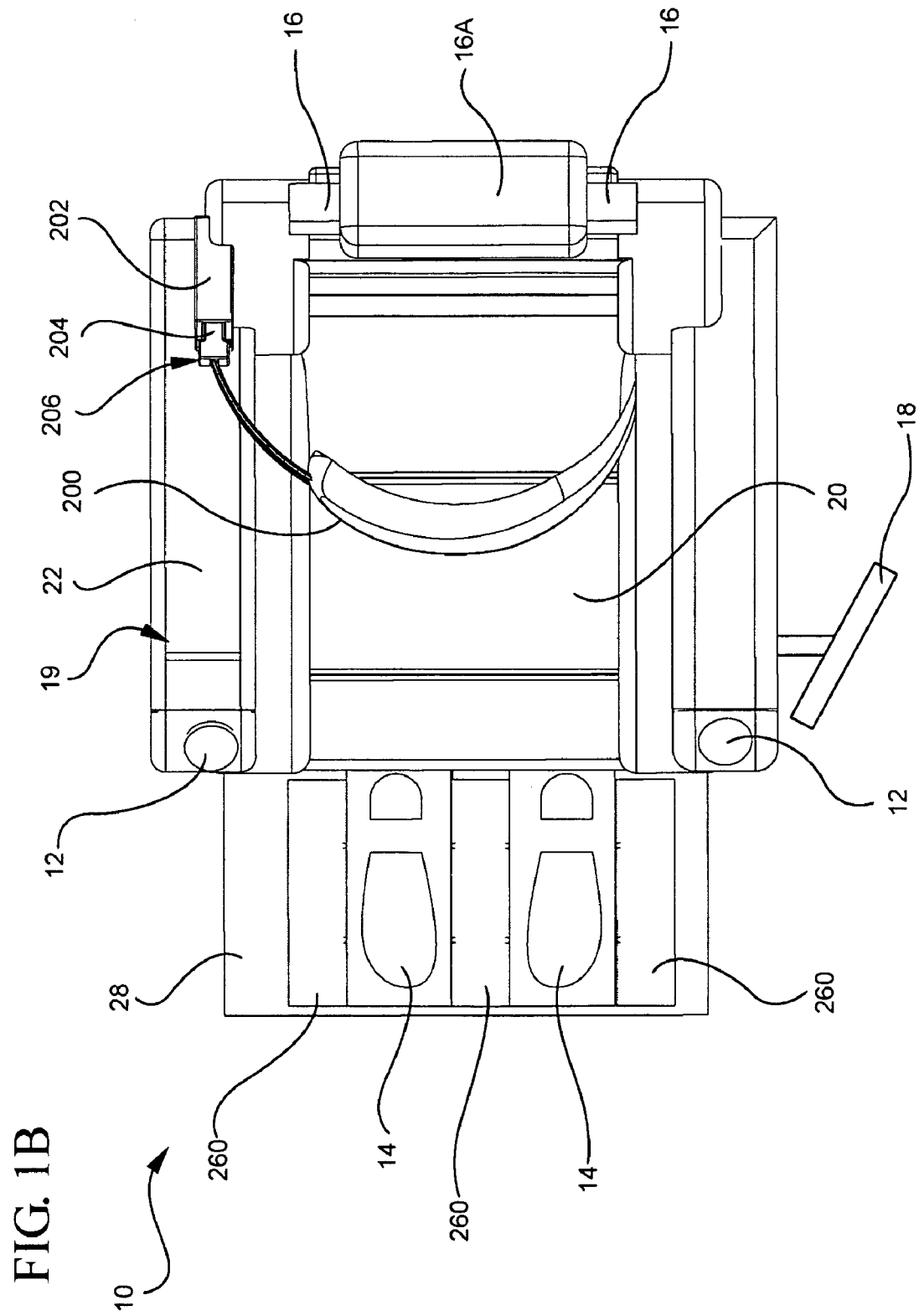
Figure 1C:
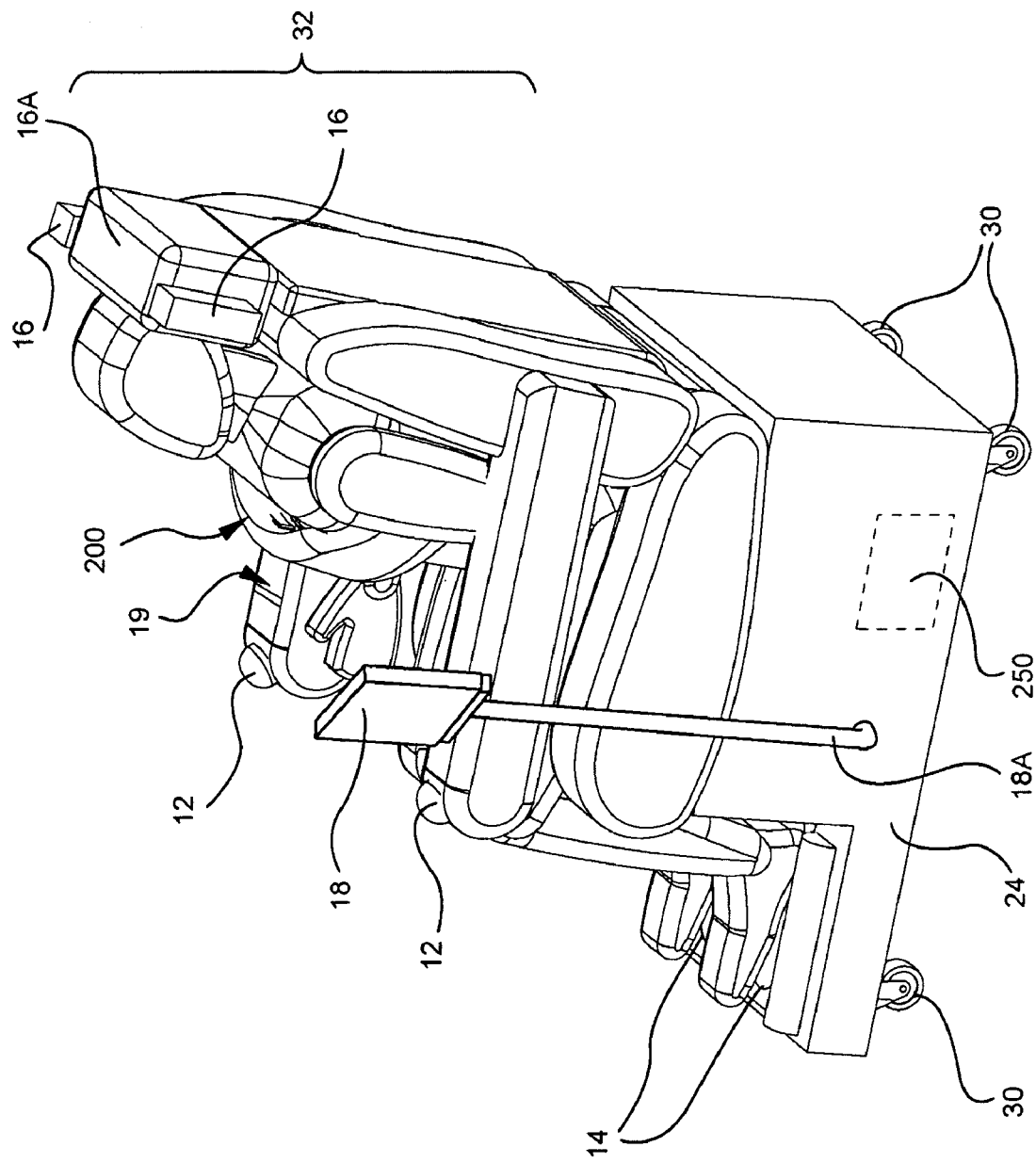

One embodiment of the monitoring device 10 in which a patient can be seated is shown in FIGS. 1A-C. The monitoring device 10 includes a support structure 32 that includes a seat portion 20, backrest section 21, arm rests 22, hand grip elements 12, foot plates 14, a hinged arm 200, and an ECG analyzer unit 250. The monitoring device 10 can be configured to facilitate 12 channel ECG measurements.

The arm rests 22 are configured to include the hand grip elements 12 and are formed from a conductive material. Preferably, the hand grip elements 12 are disposed in a front portion of the arm rests 22 such that the patient sitting on the support structure 32 can readily grasp the hand grips 12 in a comfortable position while seated. As shown in FIGS. 1A-C, the hand grip elements 12 have a spherical configuration. In other embodiments, the hand grip elements 12 can be hemispherical, rod-like, or otherwise shaped. Advantageously, the hand grip elements 12 operate as ECG transducers in that they transfer the ECG potential generated by the patient's cardiac system (shown in FIG. 2) to the analyzer unit 250 of the monitoring device 10 for analysis and display, as described in greater detail below.

Figure 8:
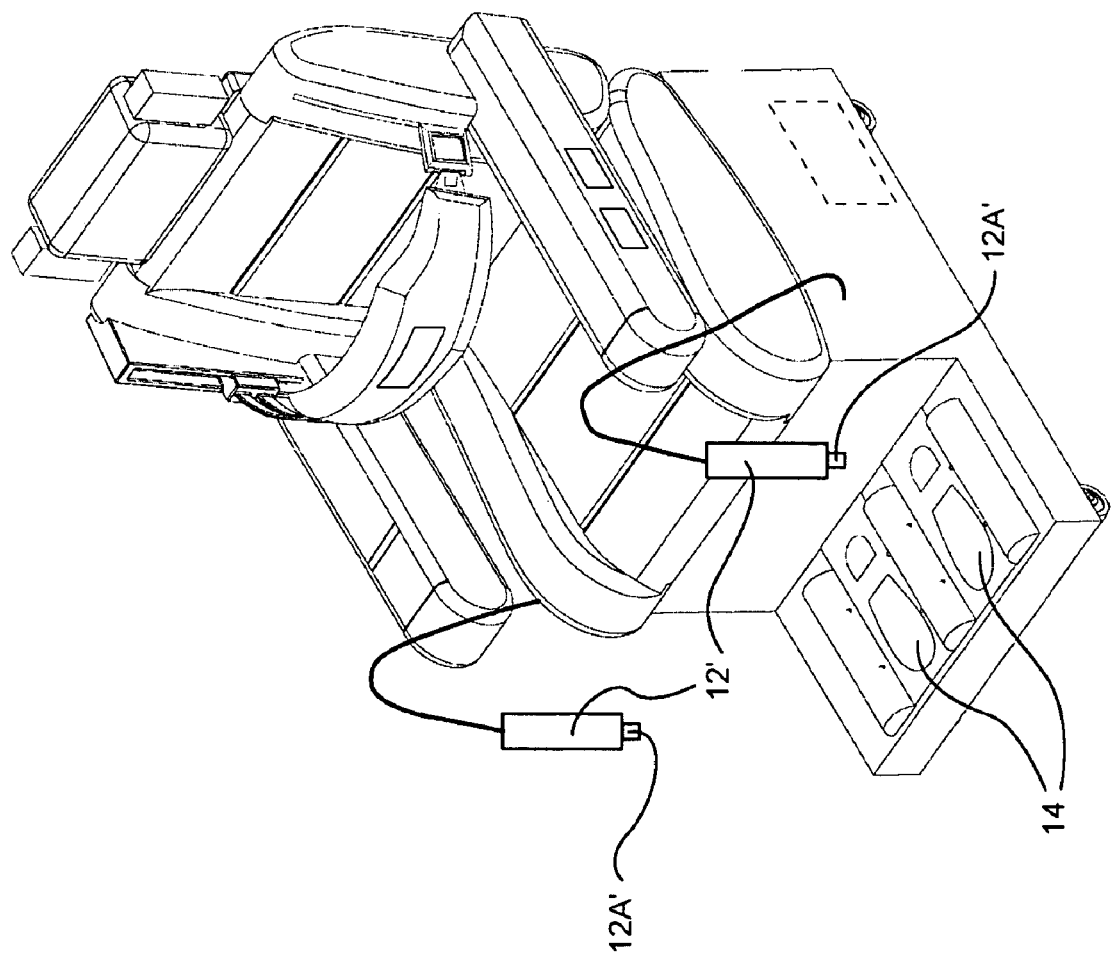
FIG. 8 illustrates hand grips according to a second embodiment of the present invention.

Various types of hand grip elements can be deployed with the present invention. For example, in one embodiment, referring now to FIG. 8, the hand grip elements 12' are shown separate from the arm rests 22 and are formed as metal bars that provide ECG measurements via arterial signals in each hand. As shown in the FIG. 8 example, in operation, the patient preferably grasps and maintains slight pressure on each of the hand grips 12' while seated. In some embodiments, the hand grips 12' are a pair of aluminum-oxide coated hand grips that incorporate a trigger handle 12A' with an electrical micro switch to signal a ready state for measuring. In some embodiments, the patient confirms the ready state by a voice activated command to the ECG analyzer unit 250. The two hand grip micro switches can be wired in series so that both switches are maintained closed for the test to continue. In some embodiments, the micro switch wiring provides data signals to a main analyzer controller input of the ECG analyzer unit and can be isolated from the main ECG measurement electrical circuitry. The hand grips 12' can be electrically connected via low impedance wiring to an input stage of the ECG analyzer unit 250. Advantageously, the hand grips 12' do not require manual cleaning after each patient use as they are part of a regular system clean program, as described in more detail below.

Referring back to FIGS. 1A-C, the support structure 32 is an electrically-adjustable chair that is provided for the patient to sit in a relaxed manner prior to commencement of the ECG test. To obtain the most accurate ECG measurement, the patient is preferably seated in a comfortable relaxed position.

The support structure can include controls 270 for adjusting a position of the support structure to achieve a comfortable, resting position. The patient can control the position of the support structure 32 using the controls 270 to adjust the support structure to a position that is comfortable for the patient to reduce or eliminate affects of discomfort on the ECG measurements. Preferably, the support structure 32 includes adjustments in rake, height, horizontal movement, and tilt. For example, using the controls 270 the user can adjust the rake of the support structure to incline or decline the back rest section 21, can adjust the height of the support structure to raise or lower the support structure 32, can adjust the horizontal position of the support structure 32 to move the support structure forward or backwards, and/or can adjust the tilt of the support structure to change an orientation of the seat 20. In some embodiments, all adjustable axes of the structure 32 preferably lock in a last set position until the patient moves the structure 32 again.

As shown in FIGS. 1A-C, the support structure 32 can be secured to a base 24 that includes lockable wheels or casters 30, such that the device 10 may be portable and readily moved from one location to another by the patient or other individual without significant effort. In some embodiments, a card reader 19 is also provided that is integrated into the arm rest 22 of the support structure 32 and a touch screen Video Display Unit (VDU) 18 on an adjustable arm 18A adjacent to the seated patient. Audio speakers 16 can be provided within a headrest 16A of the device 10. Details of the VDU 18 and speakers 16 are discussed in further detail below. The area beneath the base 24 is preferably used to store the ECG Analyzer unit 250 and other communication network devices that can be utilized to transmit ECG measurements to a host computer.

As shown in the FIGS. 1A-C example, the base 24 of the device 10 preferably includes a platform 28 that is outfitted with a pair of conductive foot plates 14 that also operate as ECG transducers and in a fashion analogous to the aforementioned hand grips 12, except using the patient's bare feet to measure the ECG potential(s). The hand grips 12 and plates 14 are insulated from ground and each other and are connected directly to the ECG analyzer unit 250. In some embodiments, the material used to form the hand grips 12 and plates 14 includes silver silver chloride (Ag—AgCl).

Figure 7:
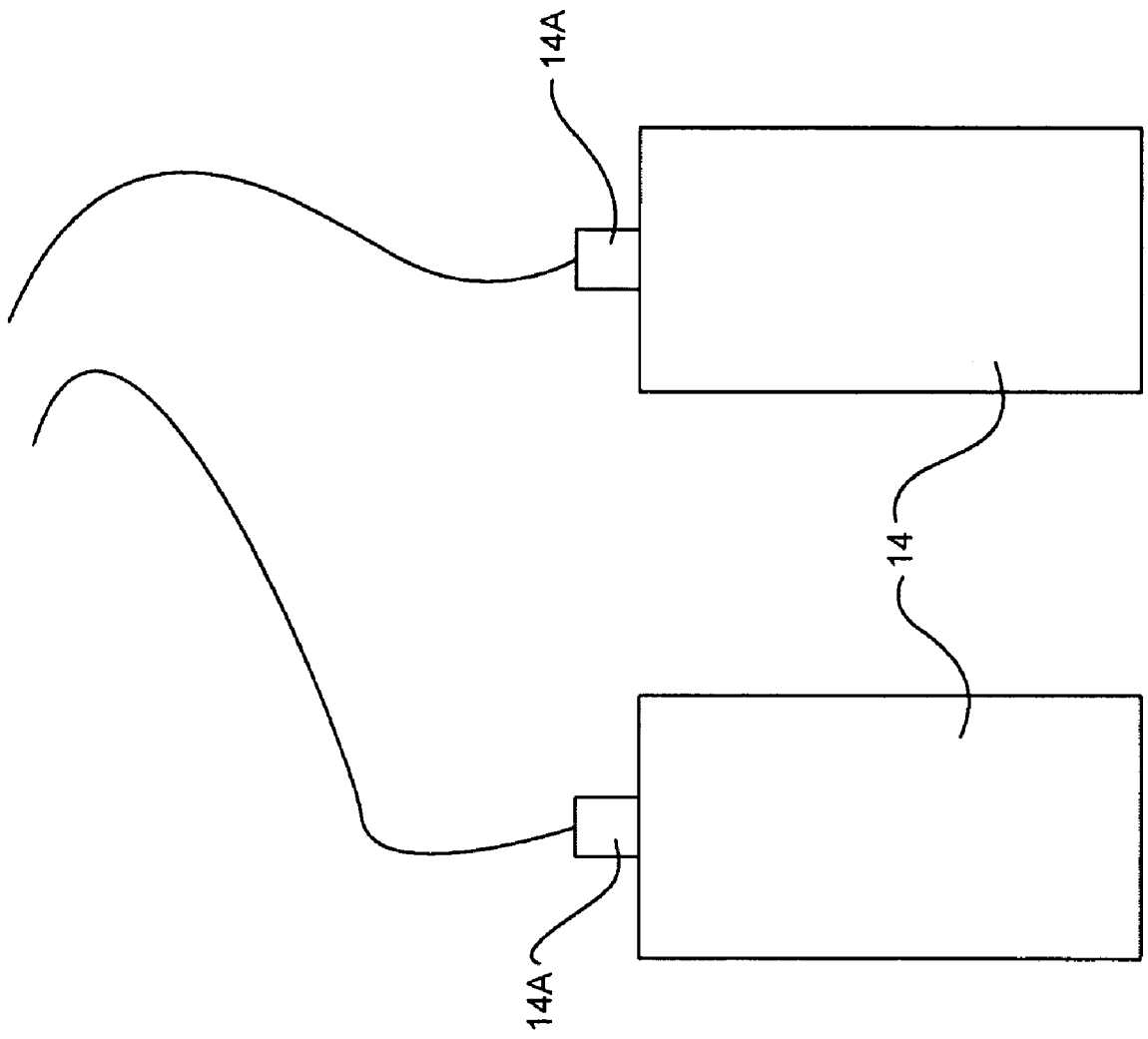
FIG. 7 illustrates foot plates according to a first embodiment of the present invention.

The foot plates 14 do not need to be deployed on the platform 28. For example, referring now to FIG. 7, the foot plates 28 can be made from two aluminum-oxide metal plates measuring about 10" long by about 4" wide and about 0.25" thick, with each having a low-impedance, bonded electrical wire connection 14A to the analyzer unit 250. The plates 14 can be insulated from the ground and from each other. The patient can be instructed to place one foot on each plate prior to the commencement of the ECG test procedure and can be reminded to maintain contact with the foot plates 14 throughout the test until completion of the ECG analysis. At the end of the ECG test, a cleaning unit 260, which can include an automated nozzle 262, can dispense an alcohol-based cleaner to spray both foot plates with the alcohol-based cleaner to substantially disinfect the foot plates and reduce the risk of cross infection. For example, the cleaning operation can be initiated upon the patient removing their personal ID card from the card reader 19 and/or upon the monitoring device 10 sensing that the patient's feet have been removed from the foot plates 14 after the ECG test procedure.

Figure 9A:
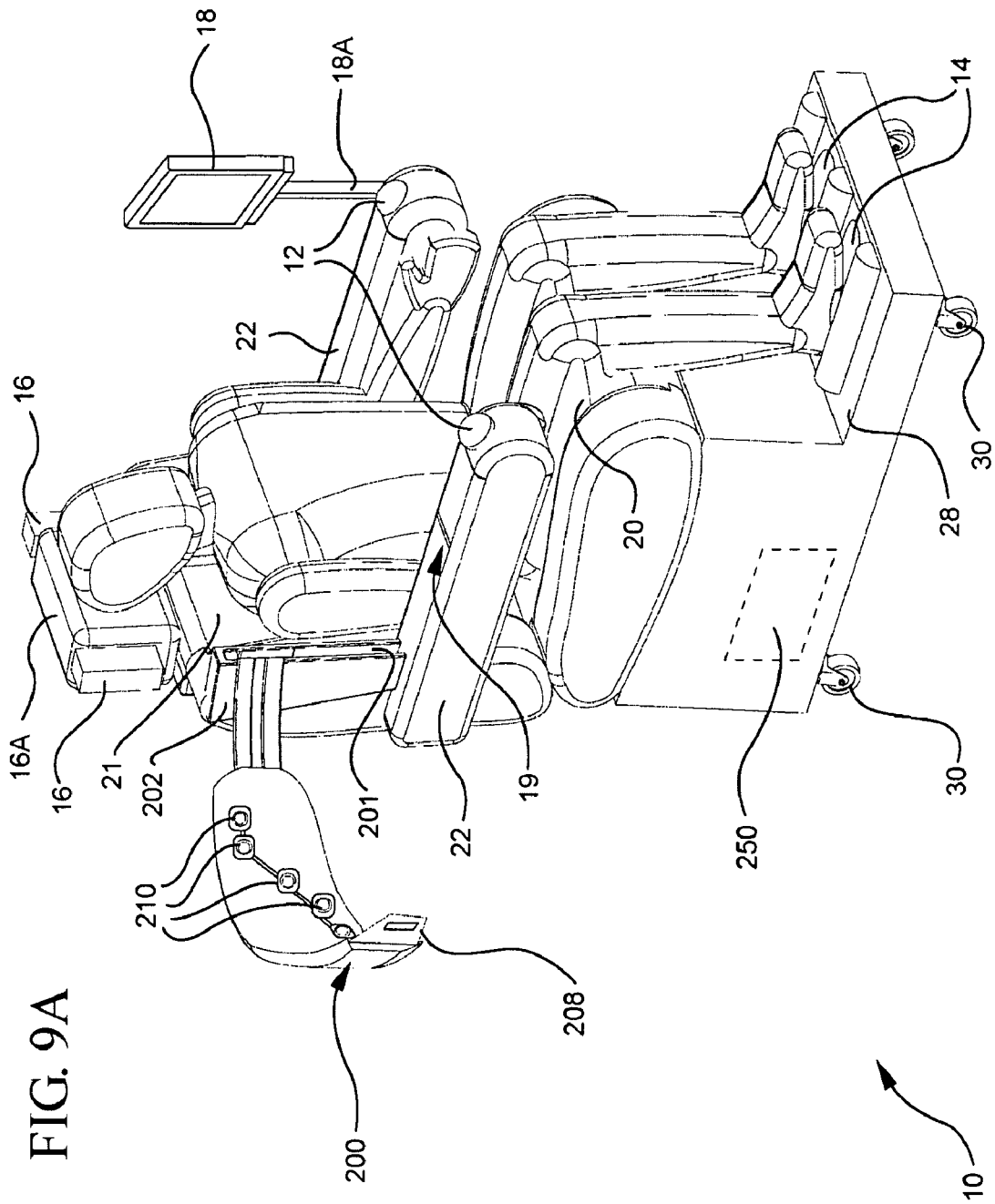
FIGS. 9A-C illustrate the hinged arm of the ECG measuring device of FIGS. 1A-C in more detail.
Figure 9B:
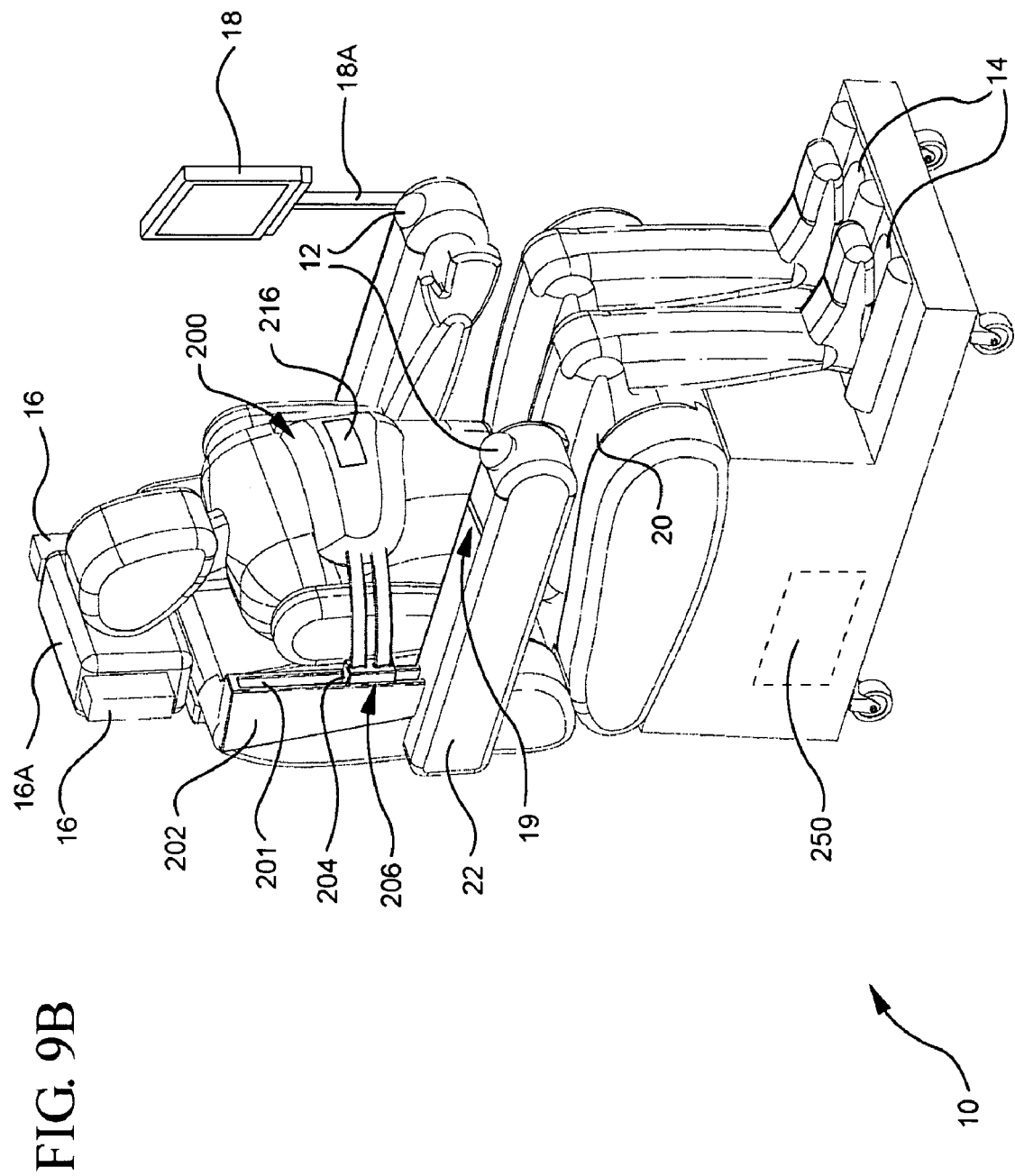

With reference to FIGS. 1A-C and FIGS. 9A-C, the hinged arm 200 of the monitoring device 10 can be operatively coupled to a shaft 202. The shaft 202 can extend vertically along the side of backrest section 21 and can include a channel 201 extending in the longitudinal direction of the shaft 202, which receives a portion of the hinged arm 200. The hinged arm 200 can be operatively coupled to the shaft 202 by a horizontal pivot bearing 204 and/or a friction bearing 206 engaged in the channel 201. The horizontal pivot bearing 204 enables the hinged arm 200 to be manually moved from a parked upright position (FIG. 9A) to a measuring position radially about the shaft 202 such that the hinged arm 200 rests above the patient's thorax and upper chest region (FIG. 9B). The hinged arm 200 can be counterbalanced and locked in place with a locking device 208, such as a locking device of a car seat belt lock.

The friction bearing 208 enables the hinged arm 200 to be displaced vertically by allowing the hinged arm 200 to slide up and down along the channel 201 of the shaft 202. The friction bearing 208 provides ease of movement without allowing the hinged arm 200 to drift downwards due to gravitation forces. The hinged arm 200 can be moved vertically along the channel 201 of the shaft 202 by the patient to align the hinged arm 200 with the patient's thorax.

Figure 9C:
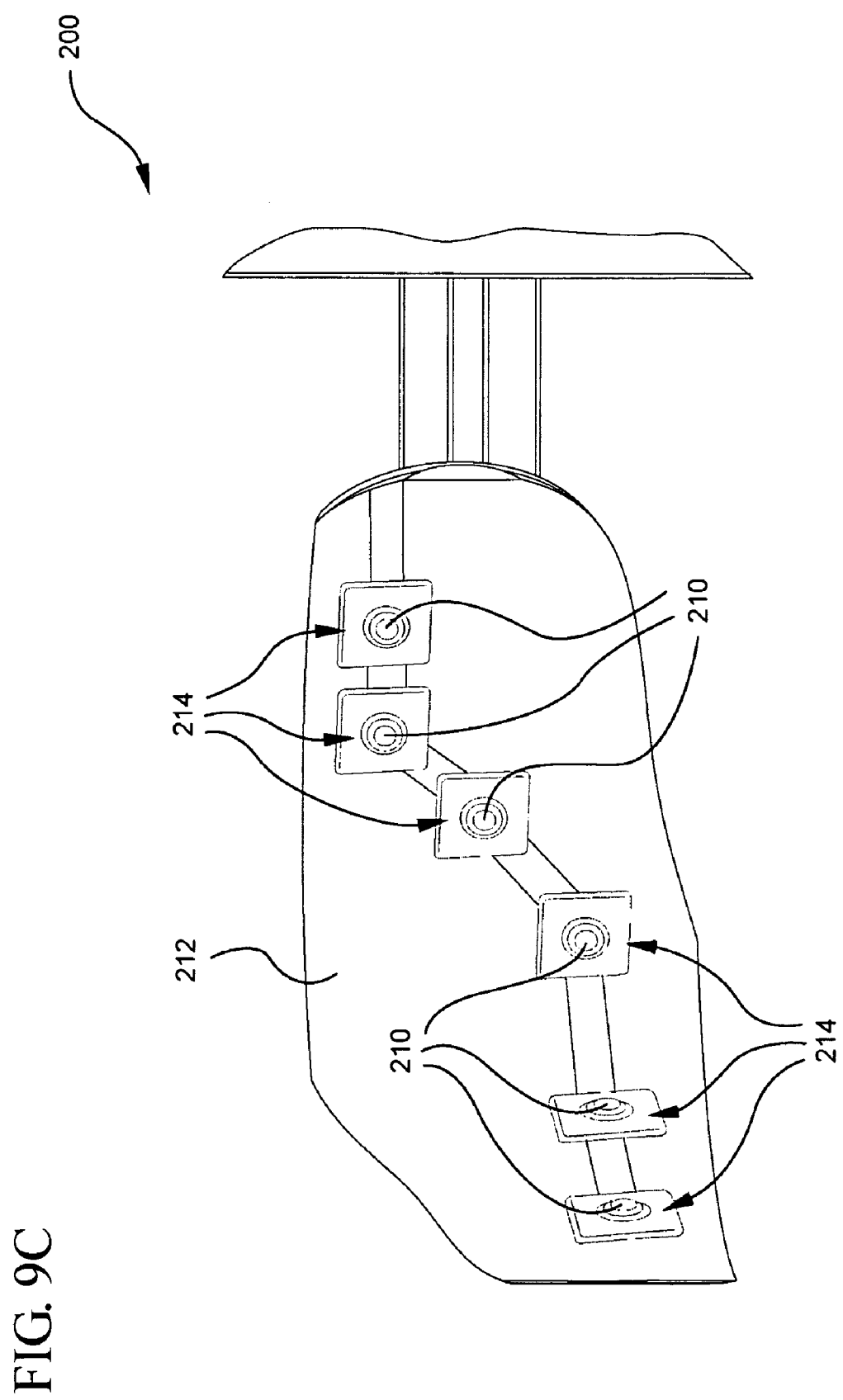

The hinged arm 200 can include ECG transducers 210, as shown in FIGS. 9A and 9C, disposed on a surface 212 of the hinged arm 200 that comes in contact with a seated patient during the ECG measurements. The hinged arm 200 is positioned by the patient to ensure ECG transducers 210 disposed on the hinged arm 200 are centered above the patient's thorax. In some embodiments, the hinged arm 200 can include six ECG transducers 210 (FIG. 9C). Four of the ECG transducers 210 can be disposed and positioned on the hinged arm 200 to facilitate alignment of the four ECG transducers with the central thorax of a patient. Two of the ECG transducers 210 can be disposed and positioned on the hinged arm 200 to facilitate alignment of the two ECG transducers with the left rib cage of the patient. Using six (6) transducers of the hinged arm 200, with two (2) foot plates 14 and two (2) hand grips 12 provides ten (10) transducers for facilitating a twelve (12) channel ECG measurement with the monitoring device 10.

The compliant inner surface 212 of the hinged arm 200 includes individual pneumatic inflatable envelopes or cells 214. Each of the cells 214 contains one of the ECG transducers 210 and associated wiring to the ECG analyzer unit 250. The complete set of cells 214 is contained in durable rubber medium, such as Viton®. When the patient has moved and locked the hinged arm 200 in place (FIG. 9B), placed their feet and hands on the appropriate metal contacts (e.g., hand grips, foot plates), and finally initiates the commencement of the ECG test via, for example, the system voice activated controls, the cells 214 are inflated via an air pump 216. The inflation of the cells 214 forces the ECG transducers 210 outward away from the hinged arm and towards the patient's thorax. This reduces the distance between the transducers 210 of the hinged arm 200 and the patient's chest thus providing a safe, compliant method of maximizing contact of the transducers 210 with the patient. When the test is completed, a two-way valve opens and the air in the cells 214 is vented to atmosphere via an exhaust filter.

Referring still to FIGS. 1A-C, the on-screen VDU 18 is mounted generally in front of the patient's body and positioned for comfortable viewing. The display 18 can be used to provide still frame or video images to the patient and/or caregiver during monitoring, textual messages between the patient and a remote location (such as a remote health care facility), and/or other types of information content provided by the analyzer.

For example, the on-screen VDU 18 can provide instructions that inform the patient at the commencement of the test to sit comfortably with their feet flat on the foot plates 14. In addition, the VDU 18 can display to the patient how to hold the hand grips 12. When the patient is in position and still, the patient is then instructed via the VDU 18 on-screen prompts and audio messaging via the speakers 16 to press both hand grip trigger switches or confirm via a voice command their ready state to initiate the ECG test procedure.

Once the patient is informed through the VDU 18 and audio speakers 16 that the ECG test is complete, the patient can proceed to the next measurement or exit the session, whichever is appropriate. In some embodiments, the card reader 19 recognizes the patient's ID and authorizes the ECG test commencement. Equally, when the card is removed from the reader 19 by the patient, the ECG procedure is terminated and the monitoring device 10 is made ready for the next patient's use. The monitoring device can link ECG measurements with information of the patients ID card so that the ECG measurements are associated with the information on the patient's card. For example, the patient ID card can include an identifier to identify the patient ID card as belonging to the patient. When the patient uses the monitoring device 10 after inserting the patient ID card into the card reader 19, the monitoring device can store the ECG measurements and the identifier so that when the ECG results of reviewed, the healthcare professional can determine that the ECG results are for the patient. In other embodiments, the patient can enter information using the VDU 18 and the monitoring device can link the information entered using the VDU 18 to the ECG measurements.

The monitoring device 10 can use wired and/or wireless communications to transmit ECG measurement information to one or more host computers. For example, the monitoring device 10 can use a wireless radio frequency transceiver arrangement to permit both freedom of movement and data to flow both from the monitoring device 10 to a host computer, such as a server, or vice-versa. A number of different wireless transmission methodologies (air interfaces) may be employed to transfer data between these entities including, inter alia, point to point transmission via the Infrared Data Association's ("IrDA") infrared based wireless transmission standard; wireless radio frequency ("RF") based local area network ("LAN") connections based on the IEEE 802.11 LAN access standard (including both frequency-hopping and direct sequence spread spectrum variants); the "Bluetooth" 2.45 GHz frequency band based wireless communication specification, and the Home RF Shared Wireless Access Protocol. The construction and operation of each of these air interfaces is well known in the communications arts, and accordingly is not described further herein. Of course, it will be appreciated by one skilled in the art that wired communication between the device 10 and a host computer is also possible.

The ECG analyzer unit 250 can include any commercially available multi-channel ECG analyzer unit, such as a six or twelve channel ECG analyzer. For example, the ECG analyzer unit used can be a Cardio Direct 12 USB manufactured by Spacelabs Healthcare, Inc. Preferably, the analyzer charts the patient's test results, is self-calibrating, and is capable of automated operation. In some embodiments, ECG measurement results are made available to the patient's medical specialist via a standard Ethernet connection to a remote computer in the medical specialist's office.

In some embodiments, the twelve channel analyzer unit's standard ECG software can be modified to negate the standard twelve (12) measurement channels and record six (6) results of ECG activity. It will be recognized that multiple approaches to obtaining ECG data from the patient can be employed that are consistent with the monitoring device 10.

As used herein, the notation '+ve' and '−ve' refer to polarity of the input channels of the analyzer.

For example, referring now to FIG. 2A, a single, Lead I scalar ECG of the type well known in the medical arts can be obtained by the present invention by having the patient place their hands around the hand grips 12 (+ve) and (−ve), which are connected to the analyzer as previously described. FIG. 2B illustrates that a Lead II scalar can be obtained by having the patient place their right hand (−ve) around one sphere grip and their left foot (+ve) on one foot plate.

Figure 4:
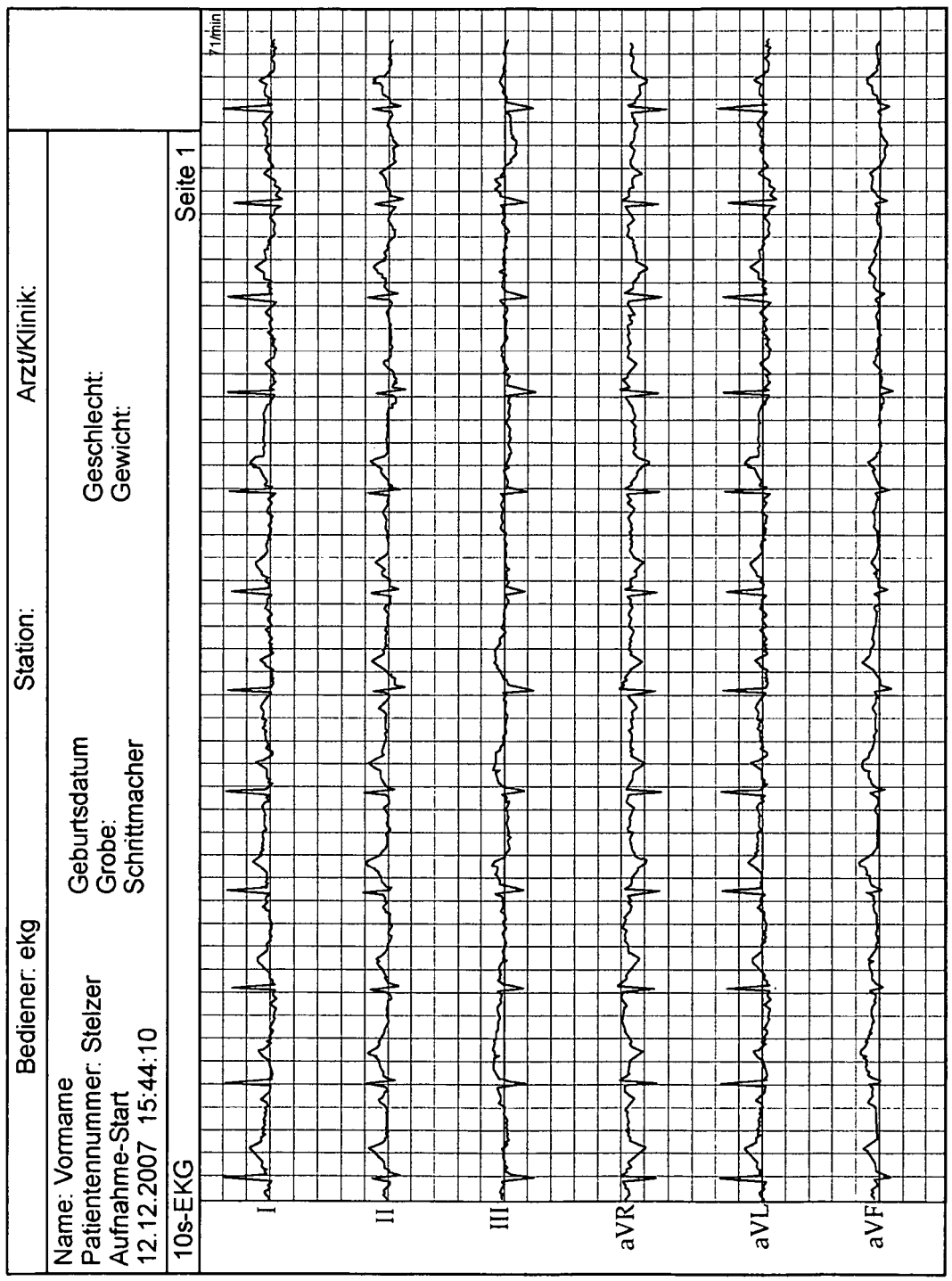
FIG. 4 illustrates example measurement results based on the connections shown in FIGS. 2A-F.

Accordingly, multiple scalar ECG leads can be obtained (up to 6) when the patient places one or more bare feet on the conductive foot plates 14 and hands on the hand grips 12. Under such situations, as shown in FIGS. 2A-F, six (6) ECG scalars can be obtained as is conventional with ECG monitoring; Leads I, II and III, and the "augmented" leads including a "aVR" lead, where the analyzer is connected between the right hand (+ve) and (−ve) measurement node with 2 programmable electrical resistors connected in parallel from the (−ve) node to the left foot and left hand, respectively, a "aVL" lead, where the analyzer is connected between the left hand (+ve) and (−ve) measurement node with 2 programmable electrical resistors connected in parallel from the (−ve) node to the right foot and right hand, respectively, and an "aVF" lead where the analyzer is connected between the left foot (+ve) and (−ve) measurement node and programmable resistors are connected in parallel from the (−ve) node to each hand respectively. Example ECG measurement results based on the connections described above are shown in connection with FIG. 4.

Figure 3:
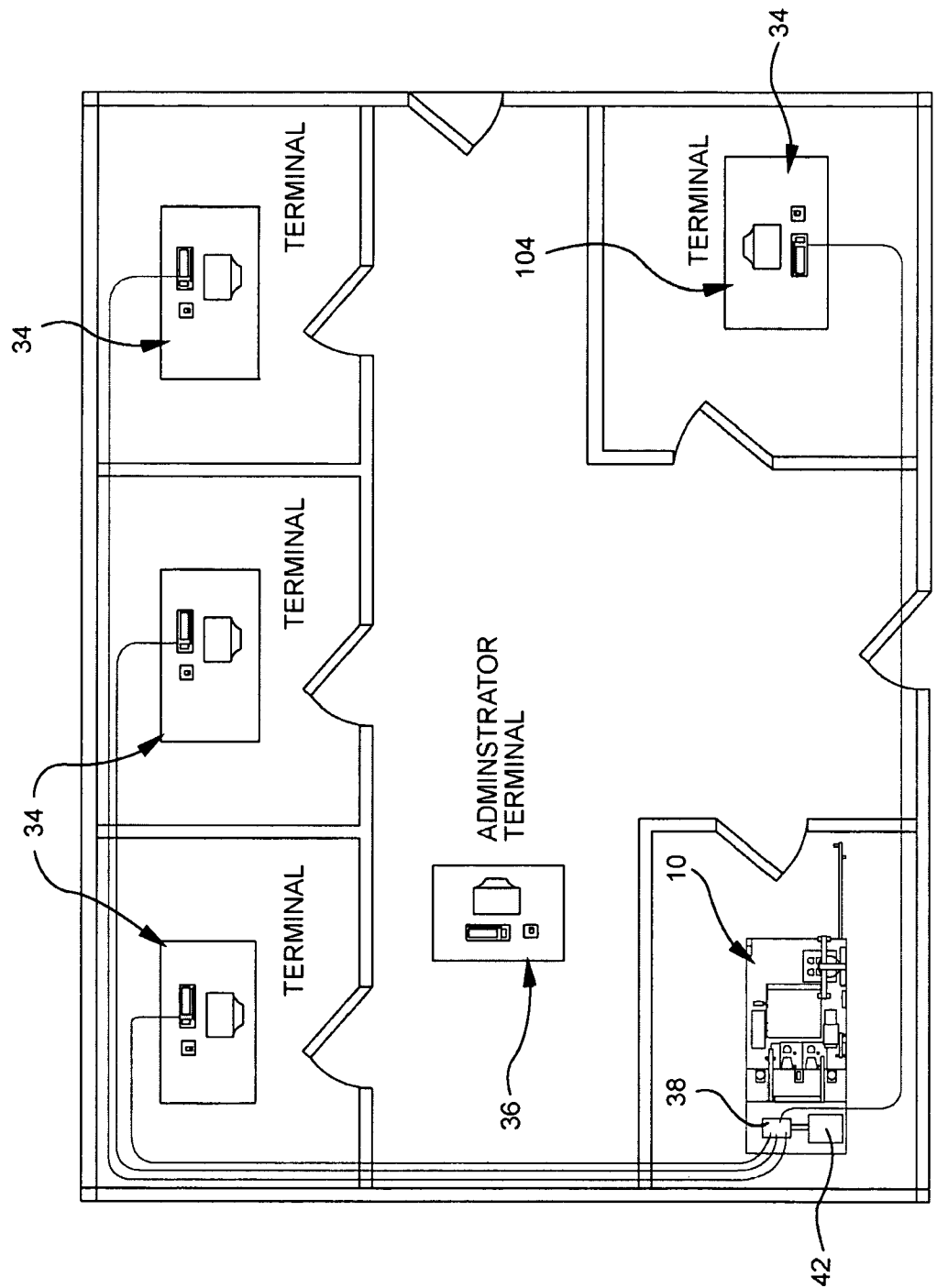
FIG. 3 illustrates a plurality of remote terminals ECG arranged for use in a medical center in accordance with the present invention.

Referring now to FIG. 3, the monitoring device 10 is suitable for installation into a doctor's medical center as a standalone, portable and self-calibrating ECG measurement unit. There would be no need for any planned medical or administrative assistance to operate the ECG device. The patient would be required to remove their shoes, boots, socks or hosiery prior to the test and would be prompted by video and audio messages as to the correct test procedure.

In one embodiment, the card reader 19 of the device preferably verifies patient identity and test authorization. The ECG results and patient's personal details would, at the completion of the test, be available for further analysis by the patient's doctor or medical specialist.

For example, as shown in FIG. 3, measurement results from the monitoring device 10 can be transmitted to a host computer 42 of a medical center using wireless and/or wired communication. One or more doctors are provided the opportunity to either monitor the test results on remote terminals 34 from their offices through an interface unit 38 before the patient leaves the medical center or examine their patient's test results on their remote terminals 34 at a later time for subsequent referral interviews with their patients. Preferably, the doctors are only able to access the test results of their own specific patients and not those of other doctors or specialists without specific authorization.

In one embodiment, a head specialist or medical center manager who has overall authorized access to the host computer 42 may be provided with authority to provide the medical information to other doctors approved by the patient through an administrator terminal 36. The patient can review their individual medical test results on the doctor's remote terminal 34, the VDU 18, or via print outs.

In other embodiments, the monitoring device 10 is integrated into a self-service patient diagnostics unit that can be deployed in a doctor's medical center or office. For example, referring now to FIG. 5, an ECG procedure could be one of several patient programmed tests that are part of a patient's primary health indicators. The ECG procedure could be authorized by a doctor as part of the normal usage of the diagnostics unit program.

Figure 5A:
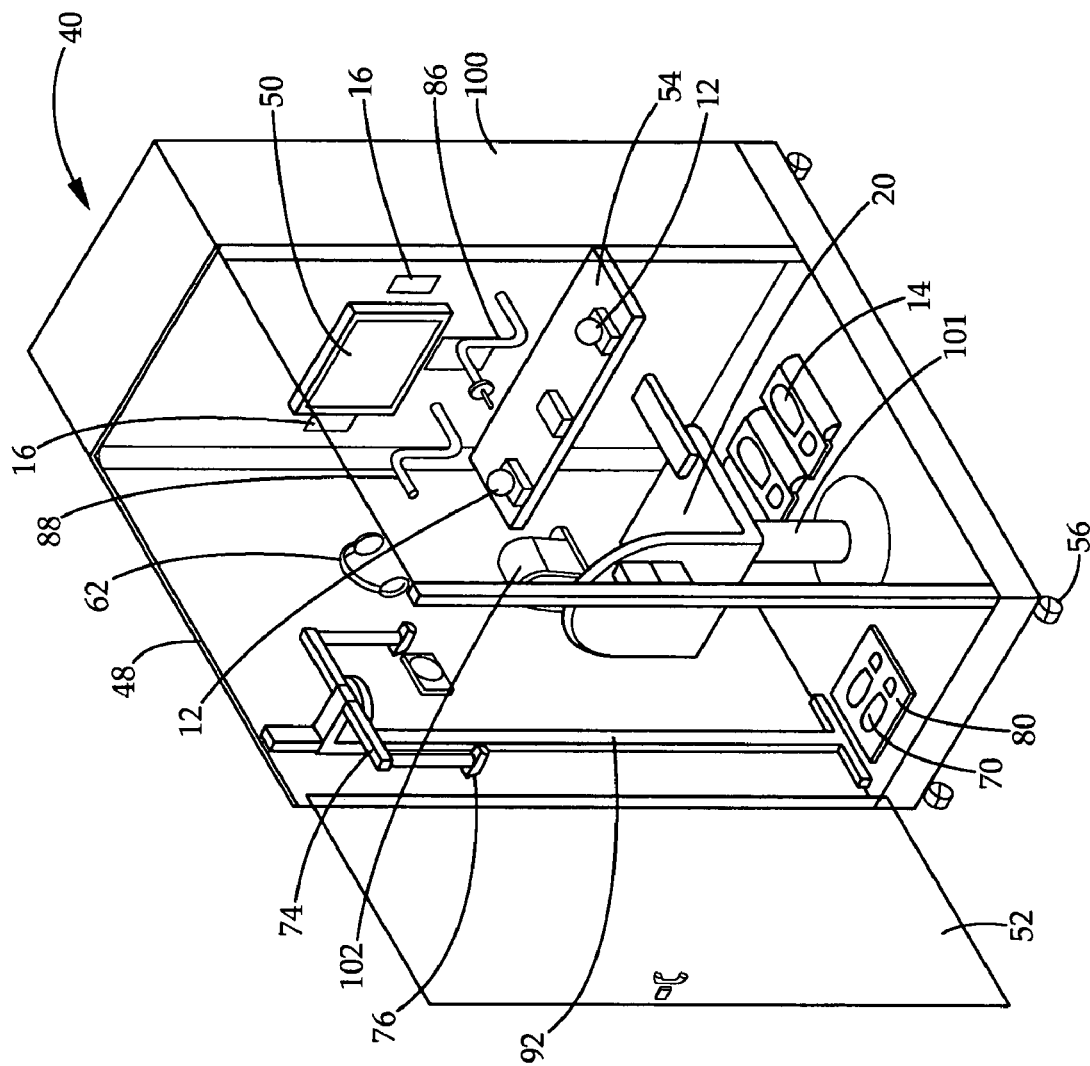
FIGS. 5A-B illustrate perspective views of an ECG measuring device according to a second embodiment of the present invention included in a medical diagnostics unit.

For example, as shown in FIG. 5A, a medical diagnostics unit 40 comprises an enclosure 48 in the form of a single occupancy booth containing either a built-in seat or chair 10' provided therein, a plurality of medical test apparatus, a touch-screen video display unit (VDU) 50 and an access door 52. The enclosure 48 can be formed from a metal frame with infill opaque side panels and equipment consoles. The consoles contain all of the appropriate medical test units for the health check measurements. A cabinet 100 of the unit also includes a host computer with hard drive storage capabilities, an interface unit to electrically connect all medical test units to the host computer and one or more network connections to all relevant remote desktop or laptop computers as described in connection with FIG. 3.

In a preferred embodiment, the medical diagnostics unit 40 is mobile and includes at least four lockable wheels 56 mounted to the bottom of the enclosure. The medical diagnostics unit 40 receives power via an earthed power cord for connection to a local 110 vac standard supply socket.

The medical diagnostics unit 40 preferably includes a wall-mounted color touch-screen visual display unit (VDU) 50, in combination with a wall-mounted loudspeaker 16 which enables the patient to access the various medical test prompt screens on the VDU 50. Initially, the patient swipes a personal ID card on a wall-mounted card reader 56 to gain access to the health check diagnostics program loaded on the host computer. The patient may also be asked to verify their identity by placing a finger digit on a local fingerprint scanner and if all details of patient identification are satisfied, the VDU 50 welcomes the patient, by name, to the test facility. If it is a first visit, the patient may be prompted to input relative patient information via the VDU 50, such as name, address, phone numbers, e-mail address and insurance carrier information or this information may have been previously input by the medical staff. Thereafter, the patient follows the visual and audio prompts to complete a series of medical tests that have been authorized for that particular session. The results of the tests are input into a patient database which can be accessed by authorized health care professionals for review and analysis. When the session has ended or the patient desires to terminate the session, the patient depresses an exit handle on the inside of the enclosure door and leaves. The door will automatically close and lock.

As described below, the patient can be prompted both visually and audibly to conduct a series of automated, self-administered tests and measurements. For example, the patient can be prompted to conduct a height measurement by a visual message on the VDU 50 to stand upright next to a labeled height gauge 92. This height gauge 92 is located inside the enclosure 48 and preferably includes a horizontal bar 74 with associated grab handles 76 for patient use. The bar 74 is attached to a vertical height scales and is preferably counterbalanced and/or has an integral locking clutch to prevent unexpected dropping of the bar mechanism.

Upon prompting by the VDU 50, the patient grips the bar handles 76 and gently pulls the bar mechanism downward until the height gauge plate that is attached to the bar mechanism makes gentle contact with the top of the patient's cranium. An integrated micro switch in the plate is then activated to record the position of the plate and height gauge. The VDU 50 confirms that the test is concluded and that the height measurement has been stored in the host computer patient data files. When the patient releases the height gauge bar mechanism, it will automatically rise, by counter weights, to a rest position ready for use by the next patient. Other arrangements for measuring height known to those skilled in the art may be used to obtain this information.

Next, the VDU 50 may instruct the patient to conduct a weight measurement. The patient stands upright with their feet on the outlined marker 70 associated with the floor mounted weight scales 80. When the patient is in position and still, the scale can automatically measure the patient's weight. Alternatively, the patient may be instructed via the VDU 50 on-screen prompts and audio messaging to press a start button located adjacent the scale. The patient can then be informed by the VDU 50 and audio messaging 16 that the weight test is completed and that they may proceed to the next sequential test or exit the session whichever is appropriate.

The VDU 50 may instruct the patient to conduct a temperature measurement. The present invention contemplates at least two alternative structures and methods. The first method includes a semi-automated body temperature reading device. A temperature thermocouple is provided that is attached to a plastic-coated flexible arm 86. The temperature sensor arm can be positioned by the patient so that the sensor tip is near to their mouth. The patient, following instructions from the VDU 50 and audio prompts 16, takes a plastic disposable cap from a dispenser in the enclosure and secures it over the end of the temperature sensor arm 86. The patient is instructed to close their lips over the disposable cap and touch a VDU 'start' button. Following a successful body temperature measurement, the patient is instructed to remove their mouth from the sensor and remove the disposable cap from the sensor tip and place the cap in the adjacent medical waste disposal chute.

The medical diagnostics unit 40 may also preferably include a lung function test apparatus 88 in the form of an air velocity transducer attached a flexible hose near to the face of the seated patient in the enclosure. Preferably, the patient is instructed by the VDU 50 and audio messaging speakers 16 to place a disposable cover over the end of the flexible hose and place the hose into their mouth and apply a nose clip. The nose clamp is preferably attached by a tether to the air velocity transducer. If desired, there may be provided a disposable cover issued for placement over the nose clamp by the patient prior to commencement of the lung function test.

The patient may also be prompted to conduct a blood pressure measurement. Specifically, the patient is instructed to sit on the chair seat 20 provided in the medical diagnostics unit 40 and follow the visual prompts on the system's VDU 50. The patient inserts their arm into and through an automated blood pressure measuring unit 102 located on an arm rest of the chair. The patient initiates the test by touching a 'start' button on the VDU 50. The application of external arterial pressure is fully automated and the pressure profile mimics that normally generated by a doctor's manual blood pressure test. If, at any time, the patient desires to stop the test, they are able to press a 'release' button on top of the blood pressure unit and the system test is terminated.

Following a successful measurement of the patient's diastolic and systolic blood pressure readings, an automatic cuff fully releases the pressure on the patient's arm and the patient is instructed by the VDU 50 to remove their arm from the test unit 102. The blood pressure results are stored in the host computer patient's file and are made available for the patient's doctor to review and analyze.

Figure 5B:
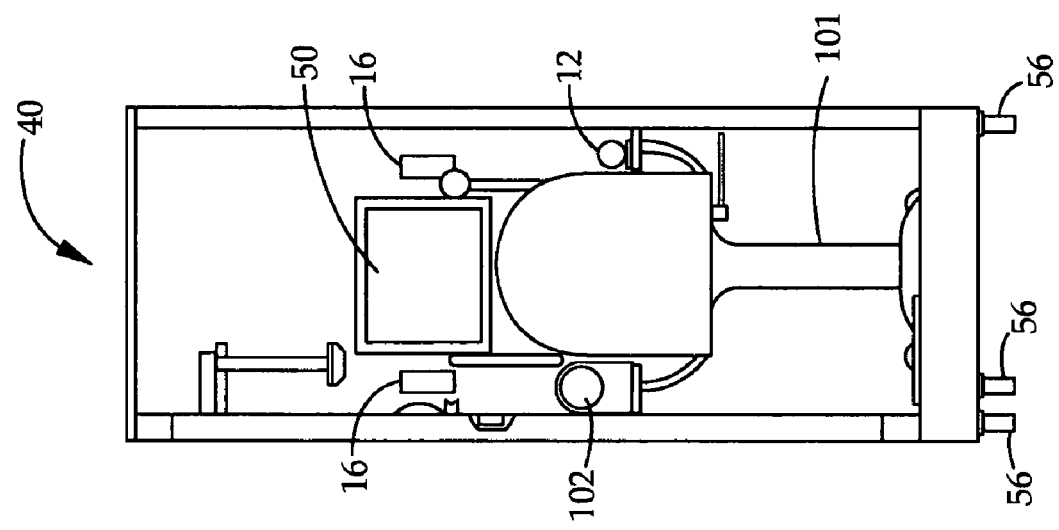

As shown in FIGS. 5A-B, the medical diagnostics unit 40 is also capable of measuring a patient's electrocardiogram (ECG) and incorporates the moniting device 10 having the ECG transducers, i.e., spherical and/or hemispherical hand grips 12, foot plates 14, and hinged arm 200 described previously. The ECG transducers can either be hard-wired to the ECG analyzer unit 250 or have a wireless connection to the ECG analyzer unit 250 and operate in the same fashion as described previously.

As discussed above, the medical diagnostics unit 40 can include a plurality of individual test units. Accordingly, the test units provided in the diagnostics unit 40 may be any known device which can obtain desired patient information and such test units are contemplated to fall within the scope of the present invention.

Figure 10A:
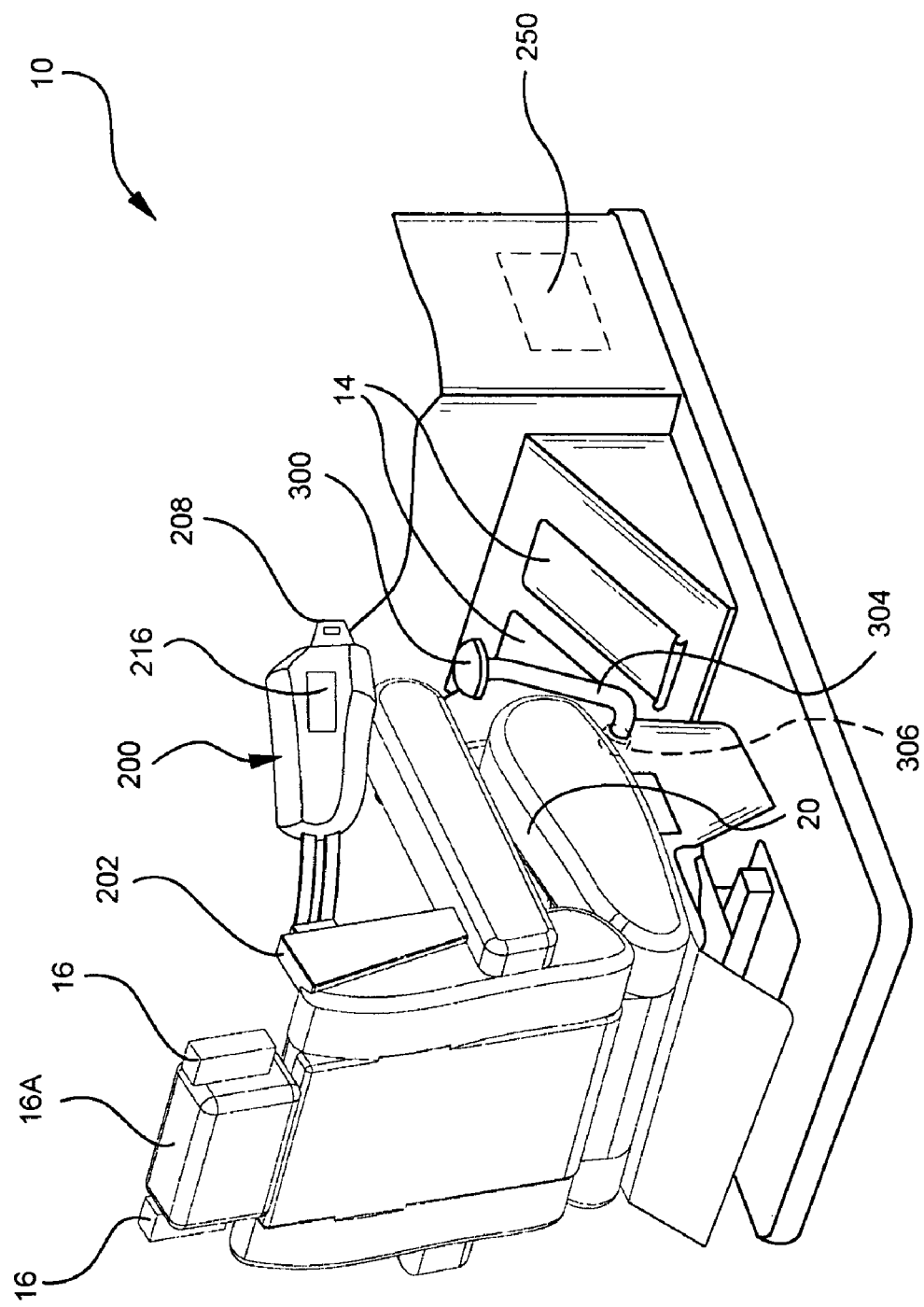
FIGS. 10A-B illustrate an exemplary embodiment of an ECG measuring device including pivoting and telescoping transducers.
Figure 10B:
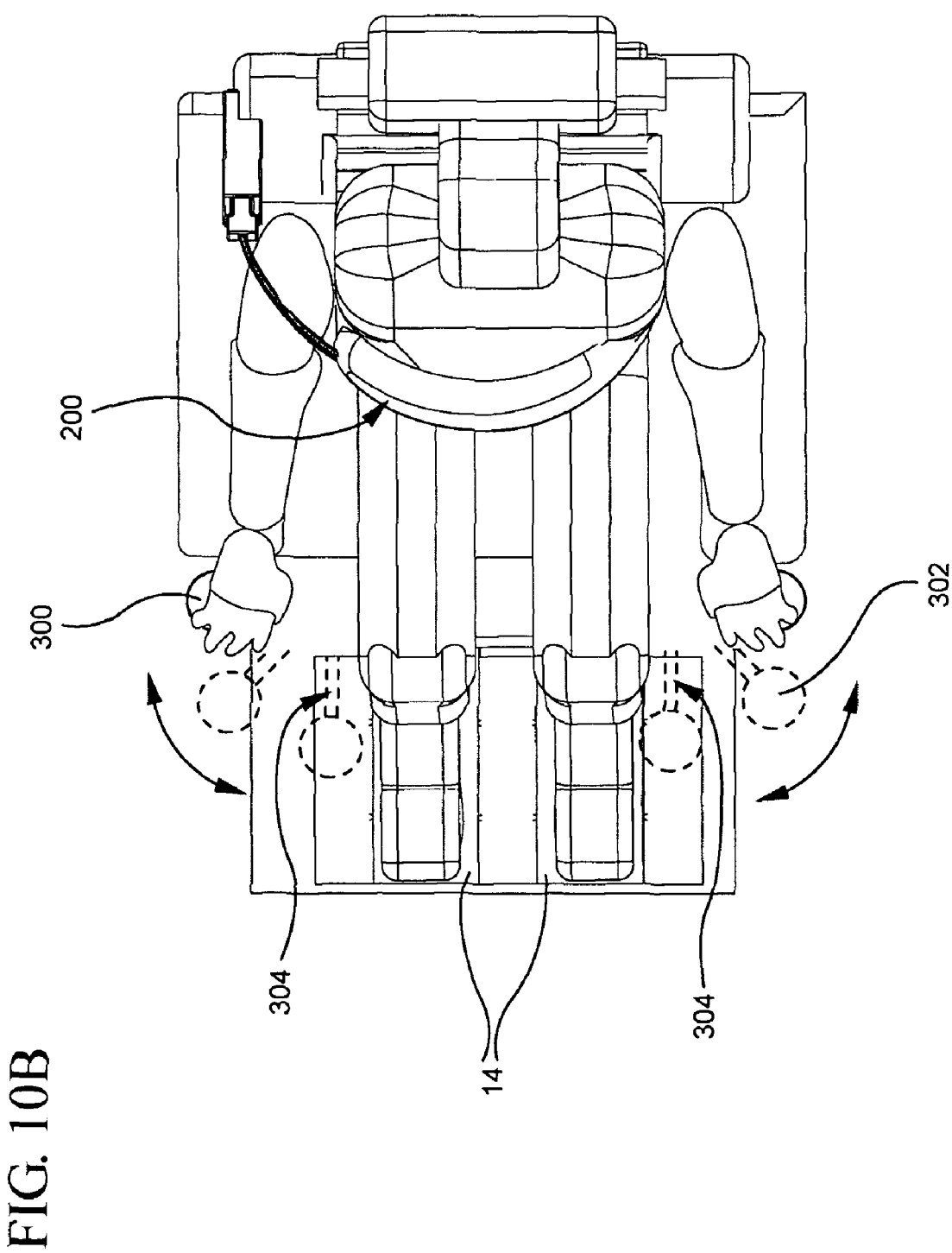

Referring to FIGS. 10A and 10B, an exemplary embodiment of the monitoring device 10 is shown that includes foot plates 14, hinged arm 200, and hand grips 300 and 302 forming transducers. The hand grips 302 and 304 preferably have a hemispherical or spherical configuration. During the ECG test, the patient rests his/her palms on the hand grips 300 and 302. The hand grips 300 and 302 are pivotally and telescopically mounted to an underside of the chair seat 20 via arms 304. The arms 304 can be operatively coupled to the underside of the seat 20 by hinges 306 such that the arms 304 can move radially about the hinges 306 resulting in the hand grips 300 and 302 being able to move laterally about a seat 20. The arms 304 can also be telescopically configured so that the patient can push the hand grips 300 and 302 away from the seat 20 to a position that allows the patient to comfortably rest his/her arms while the ECG test is being performed.

Figure 6A:
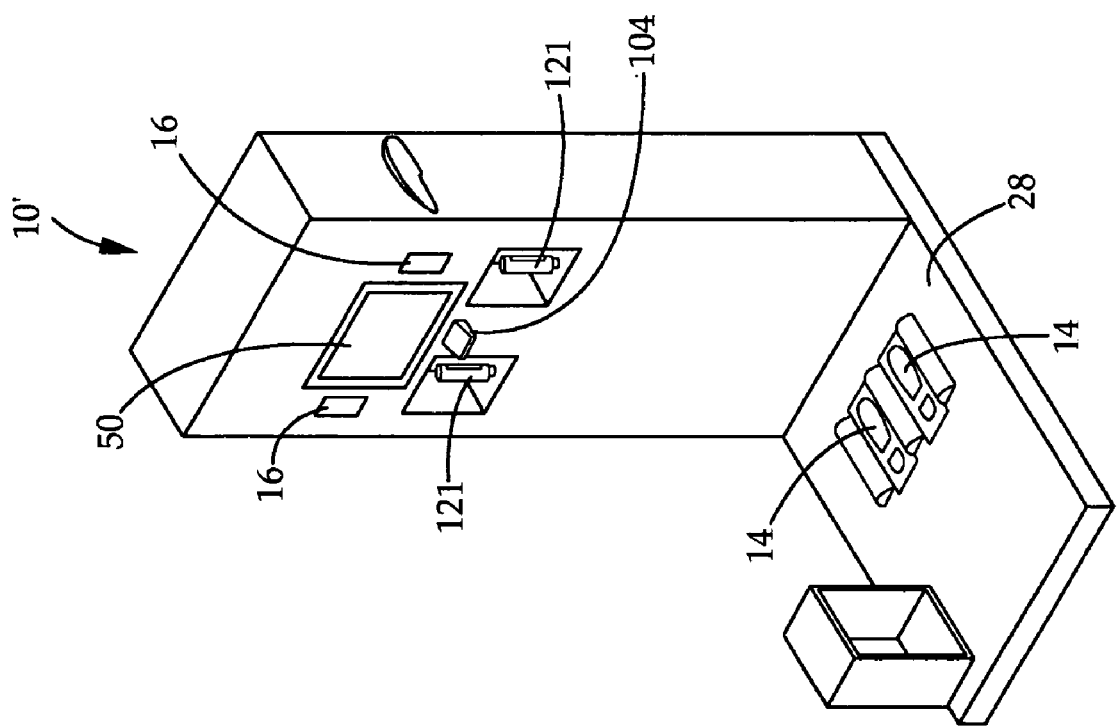
FIGS. 6A-C illustrate perspective views of an ECG measuring device according to a third embodiment of the present invention.
Figure 6C:
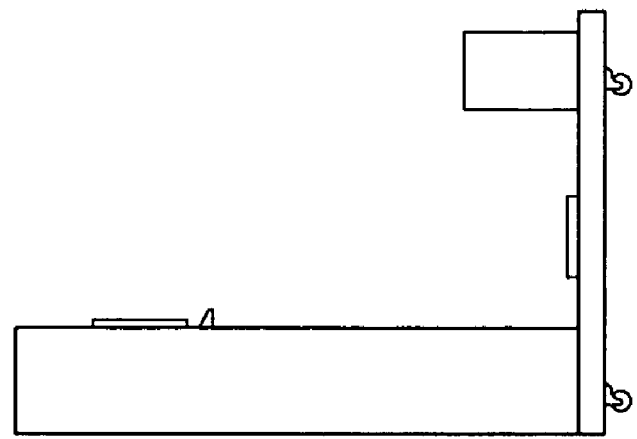
Figure 6B:
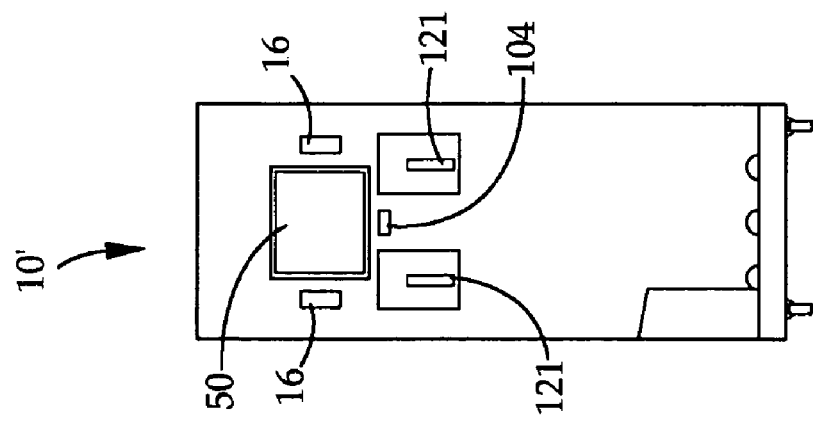

It will be further appreciated by one skilled in the art that the present invention is not limited to embodiments upon which a patient is seated. For example, referring now to FIGS. 6A-B, a third embodiment of the present invention is disclosed. As shown in FIGS. 6A-B, a portable measuring device 10' is disclosed that includes foot plates 14 mounted on a base 28' operating as ECG transducers, a plurality of hand grips 12' in the shape of bars, a card reader 104, VDU 50, and mounted speakers 16, all of which are electronically interconnected and operate in a similar fashion as described previously in connection with FIGS. 1-5 and 7-8.

A number of embodiments of the invention have been described. Nevertheless, it will be understood that various modifications may be made without departing from the spirit and scope of the invention. For example, payment terminals can provide messages to payment devices that could include information relating to upcoming offers and sales. Also, the steps described above may be modified in various ways or performed in a different order than described above, where appropriate. Accordingly, alternative embodiments are within the scope of the following claims.

What is claimed is:

1. An electrocardiogram (ECG) measuring device comprising:
   an electrically adjustable support structure configured to have a patient seated thereon during an ECG measurement;
   a plurality of hand grips operatively coupled to the support structure, the plurality of hand grips including first tactile-sensing ECG transducers for measuring ECG signals from hands of a patient, the hand grips being spaced apart and being engageable with a patient during an ECG measurement;
   a plurality of foot plates including second tactile-sensing ECG transducers for measuring ECG signals from feet of the patient, the foot plates being spaced apart from each other and from the hand grips and being engageable with a patient during the ECG measurement
   a back rest extending from the seat in a substantially vertical manner and a longitudinally extending shaft disposed on a side of the back rest;
   a hinged arm operatively connected to the support structure via a bearing, the bearing enabling the hinged arm to be displaced vertically, the hinged arm configured to be manually moved from a parked upright position to a measuring position radially about the longitudinally extending shaft, the hinged arm configured to rest above the patient's thorax and upper chest region during the ECG measurement, the hinged arm including a plurality of tactile-sensing ECG transducers disposed on an inflatable cell, the inflatable cell configured to inflate during the ECG measurement to force the tactile sending transducers of the hinged arm outward and away from the hinged arm to facilitate sufficient contact between the tactile-sensing transducers and the patient for performing the ECG measurement, the hinged arm including a locking device for securing the hinged arm in a measurement position and retaining a patient between the back rest and the hinged arm to facilitate contact between the tactile-sensing transducers of the hinged arm and the thoracic region of the patient;
   a system configured to provide at least one of visual and audio instructions to the patient for replacing the need for the presence of a medical attendant during the ECG measurement; and
   an ECG analyzer unit in communication with the hand grips and the foot plates to receive both said ECG signals from the patient in contact with the first and second transducers, the ECG analyzer unit compiling and generating a chart of ECG information based on at least one of the ECG signals received.

2. The ECG measuring device of claim 1, wherein the support structure includes an arm rest configured to include at least one of the hand grips.

3. The ECG measuring device of claim 1, wherein the hand grips have at least one of a spherical, hemispherical, and bar-like configuration.

4. The ECG measuring device of claim 1, wherein at least one of the ECG transducers are made from silver silver chloride (Ag—AgCl).

5. The ECG measuring device of claim 1, wherein the system includes a video display unit to display the visual instructions to the patient, the video display operatively connected to the ECG analyzer.

6. The ECG measuring device of claim 1, wherein the system includes at least one speaker to communicate the audio instructions to the patient, the at least one speaker operatively connected to the ECG analyzer.

7. The ECG measuring device of claim 1, further comprising a cleaning unit for dispensing a cleaning fluid on at least one of the foot plates and hand grips to disinfect the at least one of the foot plates and hand grips upon completion of the ECG measurement.

8. The ECG measuring device of claim 1, further comprising a cleaning unit in proximity with the foot plates, the cleaning unit applying a cleaning fluid to at least one of the foot plates to substantially disinfect the foot plates upon completion of the measurement.

9. An electrocardiogram (ECG) measuring device comprising:
   an electrically adjustable support structure configured to have a patient seated thereon during an ECG measurement;
   a plurality of hand grips operatively coupled to the support structure, the plurality of hand grips including first tactile-sensing ECG transducers for measuring ECG signals from hands of a patient, the hand grips being spaced apart and being engageable with a patient during an ECG measurement;

a plurality of foot plates including second tactile-sensing ECG transducers for measuring ECG signals from feet of the patient, the foot plates being spaced apart from each other and from the hand grips and being engageable with a patient during the ECG measurement;

a hinged arm operatively connected to the support structure, the hinged arm including a plurality of third tactile-sensing ECG transducers in communication with the ECG analyzer unit, the hinged arm configured to engage a thorax of a patient during the ECG measurement;

a back rest extending from the seat in a substantially vertical manner and a longitudinally extending shaft disposed on a side of the back rest, the hinged arm being operatively coupled to the shaft; and an ECG analyzer unit in communication with the hand grips and the foot plates to receive both said ECG signals from the patient in contact with the first and second transducers, the ECG analyzer unit for compiling and generating a chart of ECG information based on at least one of the ECG signals received, wherein the shaft includes a channel formed therein and the hinged arm operatively engages the channel to facilitate vertical movement of the hinged arm along the channel.

10. The ECG measuring device of claim 9, wherein the hinged arm is configured to pivot radially about the shaft.

11. An electrocardiogram (ECG) measuring device comprising:

an electrically adjustable support structure configured to have a patient seated thereon during an ECG measurement;

a plurality of hand grips operatively coupled to the support structure, the plurality of hand grips including first tactile-sensing ECG transducers for measuring ECG signals from hands of a patient, the hand grips being spaced apart and being engageable with a patient during an ECG measurement;

a plurality of foot plates including second tactile-sensing ECG transducers for measuring ECG signals from feet of the patient, the foot plates being spaced apart from each other and from the hand grips and being engageable with a patient during the ECG measurement; and an ECG analyzer unit in communication with the hand grips and the foot plates to receive both said ECG signals from the patient in contact with the first and second transducers, the ECG analyzer unit for compiling and generating a chart of ECG information based on at least one of the ECG signals received, the support structure including a seat for receiving the patient seated thereon, wherein hand grips are pivotally coupled to an underside of the seat via arms, the hand grips being configured to be pivotally positioned about the seat, each arm having a telescopic configuration to facilitate lateral extension of the hand grips away from the seat.

12. A method of measuring and recording electrocardiographic (ECG) signals, the method comprising:

providing a support structure including a seat on which a patient is seated, the support structure being electrically adjustable by the patient;

adjusting, electrically, a position of the support structure in response to input from the patient to achieve a comfortable, relaxed position, the support structure including a plurality of hand grips and a plurality of foot plates, the hand grips and foot plates operatively coupled to the support structure, the hand grips being pivotally coupled to an underside of the seat, the adjusting of the position of the support structure including pivoting the hand grips about the seat;

acquiring ECG information representing a heart function of a patient from the plurality of hand grips in contact with hands of the patient and from the plurality of foot plates in contact with feet of the patient, the hand grips and foot plates including tactile-sensing ECG transducers, the foot plates and hand grips being spaced apart from each other;

storing the ECG information to a database; and charting the ECG information received from the hand grips and foot plates to display a result of the ECG measurement.

13. The method of claim 12, further comprising transmitting the electrocardiographic signals to a host computer, the host computer displaying the result of the ECG measurement.

14. The method of claim 12, further comprising:

reading patient information from a patient ID card before commencement of the ECG measurement; and linking the patient information read from the patient ID card with the ECG information that is acquired.

15. The method of claim 12, further comprising acquiring ECG information representing a heart function of a patient from a plurality of tactile-sensing ECG transducers engageable with a thorax region of the patient during the ECG measurement.

16. The method of claim 12, further comprising applying a cleaning fluid to at least one of the ECG transducers upon completion of the measurement.

17. The method of claim 12, further comprising telescopically adjusting an arm supporting the hand grips.

* * * * *